United States Patent [19]

Wang

[11] Patent Number: 5,407,638

[45] Date of Patent: Apr. 18, 1995

[54] DETECTOR-CELL ADAPTED FOR CONTINUOUS-FLOW ABSORPTION DETECTION

[75] Inventor: Priestley J. Wang, Houston, Tex.

[73] Assignee: Shell Oil Company, Houston, Tex.

[21] Appl. No.: 53,785

[22] Filed: Apr. 28, 1993

[51] Int. Cl.⁶ ............................................. G01N 21/05
[52] U.S. Cl. ................... 422/82.09; 250/576; 356/246; 422/81; 422/82.05; 422/82.06
[58] Field of Search .................... 422/81, 82.05, 82.06, 422/82.09, 91; 436/164, 52; 356/213, 246, 436, 440; 250/432 R, 435, 576

[56] References Cited

U.S. PATENT DOCUMENTS

| | | | |
|---|---|---|---|
| 2,980,512 | 4/1961 | Petersen | 422/82.09 |
| 3,327,584 | 6/1967 | Kissinger | 356/375 |
| 3,592,607 | 7/1971 | Bruce | 422/82.09 |
| 3,666,941 | 5/1970 | Watson . | |
| 3,807,875 | 4/1974 | Fischer et al. . | |
| 3,910,701 | 10/1975 | Henderson et al. . | |
| 3,967,902 | 7/1976 | Steinberg . | |
| 4,000,990 | 1/1977 | Bingham . | |
| 4,188,126 | 12/1980 | Boisde et al. . | |
| 4,276,475 | 6/1981 | Nelson . | |
| 4,281,387 | 7/1981 | Kraft et al. . | |
| 4,321,930 | 3/1982 | Jobsis et al. . | |
| 4,473,296 | 9/1984 | Shofner et al. . | |
| 4,475,813 | 10/1984 | Munk . | |

(List continued on next page.)

OTHER PUBLICATIONS

P. K. Dasgupta et al., "Light Emitting Diode Based Flow-Through Optical Absorption Detectors." Shell Oil Company received the enclosed prepublication copy on Nov. 15, 1991. The article was subsequently accepted for publication and published in *Talanta*, vol. 40, pp. 53–74 (1993).

*Process Instruments and Controls Handbook*, Douglas M. Considine, Editor-in-Chief, McGraw-Hill Book Company, Third Edition (1985), pp. 6.63–6.73, 6.89–6.91, and 6.169–6.187.

(List continued on next page.)

Primary Examiner—James C. Housel
Assistant Examiner—Jan M. Ludlow
Attorney, Agent, or Firm—Fred S. Reynolds, Jr.

[57] ABSTRACT

A continuous-wavelength absorption detector adapted for continuous-flow detection is provided. The detector includes an electronics section, a bifurcated optical guide and a detector-cell. Each branch of the optical guide has a plurality of fibers, and at one end the branches are separated and connected to different portions of the electronics section. One of the branches is terminated next to a source for producing illumination to irradiate sample material and the other branch is terminated next to a detector for producing an absorption spectrum signal. At the opposite end of the optical guide the fibers of the two branches are combined to form a common end which is connected to the detector-cell. The detector-cell includes an approximately vertically aligned continuous-flow sample cell which is connected to a sample line and also includes a concave mirror. Within the detector-cell, the common end's fiber ends are held at a fixed location on one side of the sample cell with the concave mirror being located on the opposite side. Illumination is guided from the electronics section through its respective branch of the optical guide to the common end where the light is transmitted from the fixed location across the sample cell to irradiate the sample material. The sampling material absorbs optical energy of certain wavelengths to a greater extent than other wavelengths to provide an absorption spectrum. Portions of the illuminations are reflected back across the sample cell by the concave mirror to the fiber ends at the fixed location. Reflected light which strikes the branch fiber ends associated with the detector for producing the absorption spectrum signal is then guided to the electronics section. There, an absorption spectrum signal is produced which is proportional to the illumination intensity of the wavelengths striking the fiber ends.

16 Claims, 3 Drawing Sheets

U.S. PATENT DOCUMENTS

| | | |
|---|---|---|
| 4,565,447 | 1/1986 | Nelson . |
| 4,600,310 | 7/1986 | Cramp et al. . |
| 4,628,463 | 12/1986 | Sturrock et al. . |
| 4,631,529 | 12/1986 | Zeitz . |
| 4,637,729 | 1/1987 | Schoch ................................ 356/408 |
| 4,678,338 | 7/1987 | Kitta et al. ........................... 356/420 |
| 4,688,017 | 8/1987 | Huebner et al. . |
| 4,747,687 | 5/1988 | Hoppe et al. . |
| 4,775,794 | 10/1988 | Behmann . |
| 4,784,494 | 11/1988 | Pawliszyn . |
| 4,804,266 | 2/1989 | Barshad . |
| 4,820,045 | 4/1989 | Boisde et al. . |
| 4,940,333 | 7/1990 | Pawliszyn . |
| 4,943,159 | 7/1990 | Oetliker et al. . |
| 4,973,561 | 11/1990 | Hansen et al. ........................ 422/81 |
| 5,001,054 | 3/1991 | Wagner . |
| 5,015,843 | 5/1991 | Seitz et al. ........................ 422/82.06 |
| 5,035,505 | 7/1991 | Tsukada et al. . |
| 5,046,854 | 9/1991 | Weller et al. . |
| 5,066,097 | 11/1991 | Brandle et al. . |
| 5,073,029 | 12/1991 | Eberly et al. . |
| 5,085,499 | 2/1992 | Griffin et al. . |
| 5,119,024 | 6/1992 | Popovic et al. ..................... 356/345 |
| 5,125,747 | 6/1992 | Sayegh et al. ...................... 356/410 |
| 5,148,239 | 9/1992 | Magnussen, Jr. et al. . |
| 5,153,666 | 10/1992 | Pawliszyn . |
| 5,153,679 | 10/1992 | Gilby . |

OTHER PUBLICATIONS

J. Ruzicka et al., "Flow Injection Analyses, Part I. A New Concept of Continuous Flow Analysis," *Analytica Chimica Acta.*, 78, pp. 145–157 (1975) Elsevier Scientific Publishing Co., Amsterdam.

D. Betteridge et al., "A Highly Sensitive Flow--Through Phototransducer for Unsegmented Continuous-Flow Analysis Demonstrating High-Speed Spectrophotometry at the Parts Per $10^9$ Level and a New Method of Refractometric Determinations," *The Analyst*, vol. 103, No. 1230, pp. 897–907 (Sep. 1978).

J. Huang et al., "A Dual-Wavelength Light-Emitting Diode Based Detector for Flow-Injectin Analysis Process Analysers," *Talanta*, vol. 39, No. 6, pp. 589–192 (1992).

E. A. G. Zagatto et al., "Compensation of the Schlieren Effect in Flow-Injection Analysis by Using Dual-Wavelength Spectrophotometry," *Analytica Chimica Acta.*, 234, pp. 153–160 (1990).

V. Kuban et al., "Nitroprusside and Methylene Blue Methods for Silicone Membrane Differentiated Flow Injection Determination of Sulfide in Water and Wastewater," *Anal. Chem.*, 64, pp. 36–43 (1992).

Series 6000 Process Diode Array [brochure], Ametek Process & Analytical Instruments Division, Ametek, Inc. Newark, Delaware (1991).

Model 400 Photometric Analyzers, Bulletin P-400, Ametek Process & Analytical Instruments Division, Ameteck, Inc., Newark, Delaware (1992).

Alfa-Laval/Bran+Luebbe Market Information [brochure], Bran+Luebbe Analyzing Technologies, Elmsford, N.Y. (1992).

U.S. Patent    Apr. 18, 1995    Sheet 1 of 3    5,407,638
FIG.1A
(PRIOR ART)
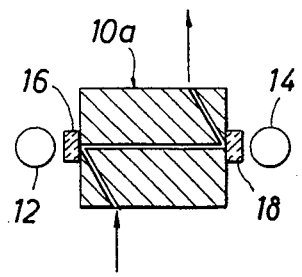
FIG.1B
(PRIOR ART)
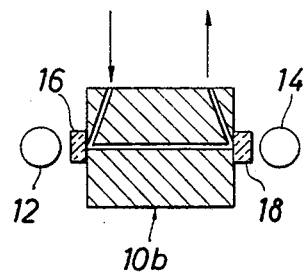
FIG.1C
(PRIOR ART)
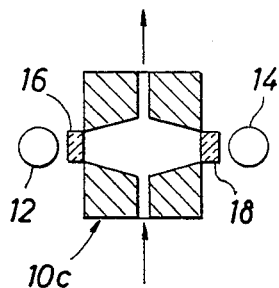
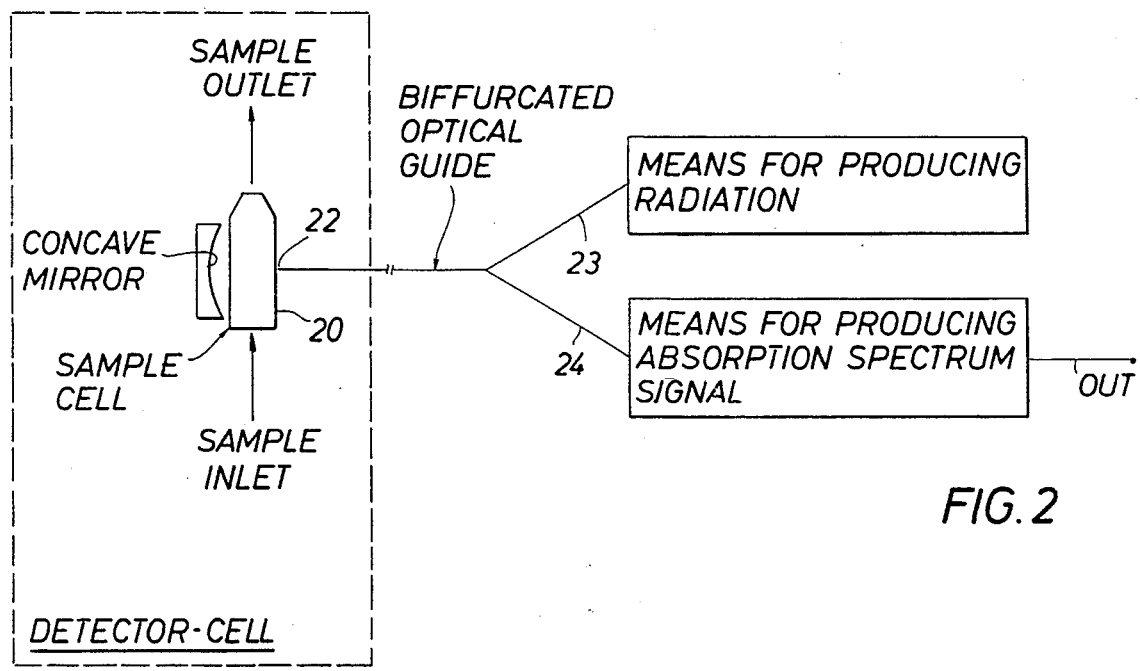
FIG.2
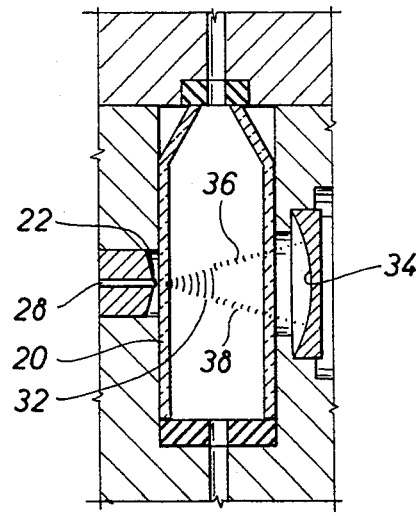
FIG.3

DETECTOR-CELL ADAPTED FOR CONTINUOUS-FLOW ABSORPTION DETECTION

BACKGROUND OF THE INVENTION

1. Field of the Invention

This invention relates to spectroscopic chemical analysis and more particularly to flow cells (sample cells) of flow-through optical detectors which are used in continuous-flow analysis, flow injection analysis, colorimetry and liquid and gas chromatography.

2. Description of the Related Art

Developments in the techniques and methodologies of chemical analysis have advanced rapidly over the last several years, especially for laboratory spectrophotometers; however, the evolution of state-of-the-art hardware designed specifically for obtaining the spectral characteristics of sample material subjected to illumination in continuous-flow analysis, FIA (flow injection analysis), colorimetry or HPLC (high performance liquid chromatography) has lagged far behind. Currently, obtaining an absorption spectrum from a continuous-flow sample system is done with complex, bulky instruments which may have inherent design limitations that increase the cost of sampling and/or reduce the performance of the detector.

In this specification, continuous-wavelength, absorption detection is the obtaining of a spectrum over a bandwidth of interest for quantitative analysis. The spectrum represents the transmittance or absorbance of the source radiation (illumination) after it has been subjected to the sample material. The bandwidth may fall within the optical range (visible spectrophotometric analysis); thus, this specification includes the area of optical detection; however, the methods and apparatus discussed herein may also apply to absorption detection in the ultraviolet (ultraviolet spectrophotometric analysis) and the infrared region (near-infrared and infrared spectrophotometric analysis) as well as the previously mentioned visible region of the spectrum. In addition, the methods and apparatus discussed herein may also apply to dual-wavelength absorption detection wherein a measuring wavelength and a reference wavelength are utilized for the absorption analysis instead of using an absorption spectrum.

A typical simple spectrophotometer (absorption detector) includes an electromagnetic radiation source, a radiation detector, a sample cell (sample chamber) and a monochromator containing a prism or grating system which dispenses the source radiation so that only a limited wavelength, or frequency, range is allowed to irradiate the sample at a time to produce an absorption spectrum for detection by the radiation (illumination) detector. In this specification the terms "illumination or radiation detector" will be used to avoid confusion with the term "absorption detector". The illumination detector converts the illumination into an electrical signal representative of the absorption spectrum. In another typical embodiment, all wavelengths of the source radiation simultaneously irradiate the sample. The absorption spectrum is dispersed such that it may either be detected by passing a limited bandwidth range of the spectrum over the radiation detector at a time or by spreading the absorption spectrum over a radiation detector acting as an array. The array detector provides an individual output signal for each limited wavelength range. Other methods are also well known to practitioners of the art for producing electromagnetic radiation (illumination) to irradiate a species and for producing an absorption spectrum signal representative of the absorption spectrum of the species which has been subjected to that illumination. Any of these methods may appropriately be applied to the teachings of this invention. However, although there are various means for producing illumination and detecting an absorption spectrum, many of these systems may not have the ability to detect absorption spectra efficiently and accurately due to inherent design limitations associated with the use of typical flow cells (sample cells).

Prior art FIGS. 1A, 1B and 1C illustrate, in simplified form, arrangements used within spectrophotometers for producing electromagnetic radiation to irradiate a sample material (species) in a continuous-flow detector-cell and for detecting an absorption spectrum. The term "detector-cell" in this specification includes a sample cell and the components associated with it. These associated components enable: (1) the source radiation to enter the sample cell to irradiate the sample, (2) the absorption spectrum to exit the sample cell for detection, and (3) the sample material (species) to enter the sample cell as a continuous-flow.

FIG. 1A is a simplified representation of a detector-cell having a continuous-flow sample cell $10a$ located between a means for producing radiation (optical energy) 12 and a means for producing an absorption spectrum signal 14. In this arrangement, optical energy is transmitted inline with the sample flow. The length of the optical energy path within the sample cell determines the sensitivity of the absorption detector. The longer the optical path is within the sample cell, the greater the detector's sensitivity to differences in absorption between the wavelengths or frequencies within the bandwidth of the spectrum.

In FIG. 1A, sample cell $10a$ is shown in a vertical-longitudinal cross-sectional view. This particular sample cell $10a$ is known as a "Z" flow-through channel structure. Other channel geometries are possible for, for example, FIG. 1B illustrates in another vertical-longitudinal cross-section view, another widely used flow-through sample cell $10b$ which has a "U" structure. The directions of flow in sample cells $10a$ and $10b$ are indicated by the arrows. The optical energy enters the sample cell in each of the FIGs. at window 16 and exits by window 18.

These flow cells ($10a$ and $10b$), shown in FIGS. 1A and 1B, are commonly used, but in order for optical radiation to be transmitted inline with the flow path of the sample material, the sample has to follow a tortuous path of flow into and out of the sample cell. One frequent problem with spectrophotometers having these types of flow cells is that they are subject to bubble noise. Often the species may have entrained gas bubbles or air bubbles. Bubble noise is caused by the bubbles becoming trapped within the sample cell due to the tortuous path of the sample through the flow cell. The natural buoyancy of the bubble in the fluid may cause it to contact and to adhere to a wall of the flow cell. When the pumping system does not provide enough flow to overcome the adherence and the friction between the bubble and the wall, it may be difficult to dislodge the bubble from the flow cell. The pumping system then causes the bubble to pulsate between pumping cycles, thus causing pulsations in the illumination intensity or causing variations in the detected absorption spectra.

One solution to the bubble problem is to use another arrangement for the sample cell as shown in the vertical cross sectional view for FIG. 1C. This sample cell 10c is a straight flow-through cell aligned vertically such that the optical energy is transmitted across the cell, i.e., transverse to the flow. However, in order to maximize sensitivity, the cell is broadened to increase the optical path length. By increasing the optical path length, the volume of the cell is increased. This increases the dead zone of the sample cell. A larger dead zone requires larger volumes of sample material for adequate separation between the samples and to prevent different species from mixing within the sample cell. In addition, this enlargement also results in reducing the total number of samples that may be processed in a continuous-flow system over a given time period.

If the optical path length is decreased to reduce the volume of the cell, the sensitivity of the detector is reduced. For example, assuming everything else remains the same, if the optical path length is halved, then the amount of absorption at various absorbing wavelengths will be substantially reduced. Sensitivity is particularly important when a heavily diluted sample which does not readily absorb at the absorbing wavelengths is used. Since so little absorption occurs across the bandwidth, then it may be difficult to determine the composition of the species especially if the sample line was subject to bubble noise or other forms of noise that is present in a plant environment.

There are other limitations with the arrangements shown in FIGS. 1A, 1B and 1C. Since the means for producing the radiation 12 and the means for detecting the absorption spectrum signal 14 are on opposite sides of the flow cell 10, these arrangements may not effectively utilize the light (radiation) entering the cell, i.e., they do not exhibit high coupling efficiency for collecting the light. Radiation upon entry into the flow cell through window 16 will diffuse (fan-out). Diffusion of this light may result from many causes. Primarily, in this case, it results from a light source producing a beam of light having rays which originate from a plurality of point sources. And, all of these point sources are not aligned so that when the rays of light from each point source enter the inlet window 16, the rays are not exactly aligned with the length of the flow cell and the outlet window 18. Additionally, other forms of diffusion also occur; these forms include: (1) refraction of light as it crosses material boundaries, (2) scattering of light due to particles along the path length and (3) the tendency of light to spread out normal to its path of movement (beam spreading).

If the flow cell is narrow, as shown in FIGS. 1A and 1B, some light, due to fan-out (diffusion), may be absorbed in the walls or blocked by the walls of the flow cell. If the flow cell is wide, as shown in FIG. 1C, only a limited portion of the light upon entry into the inlet window 16 will be directed at window 18. If large amounts of optical energy are lost within the flow cell, then the detector will have a reduced ability to detect weak, e.g., strongly absorbed, illumination at the radiation detector. The weakest absorption signal that can be detected is limited by the "dark" current (noise) produced by a photodetector or photodetector array. As the illumination becomes weaker, the signal to noise ratio is reduced until a point is reached where it is not possible to distinguish between the signal produced by the weak illumination and the noise.

The signal to noise ratio between the detected illumination and the dark current may be increased by increasing the magnitude of the optical energy entering the sample cell. However, increasing the amount of light transmitted into the flow cell could also result in increasing the temperature of the sample. Sample heating could cause chemical reactions or bubbles to come out of solution resulting in the sample no longer being representative of the material from which the sample was obtained.

The windows 16, 18 of FIGS. 1A, 1B, and 1C are also sources of inherent design limitations. They may be an integral part of the flow cell or they may be removable. In any case, they become dirty or scarred from the sample material. This reduces the performance of the absorption detector. The windows must then be cleaned or replaced. Whether the windows are an integral part of the flow cell or separately attached, the windows are difficult to inspect, clean or replace in typical detector-cell arrangements.

Safety concerns related to electrical components of the absorption detector also affect the utility of this type of detector. The cost to install this absorption detection system could be expensive due to the expenditures necessary to meet fire and building codes. These safety codes are necessary because: (1) the sample cell may contain hazardous and/or explosive materials when sampling, and/or (2) the detector's electrical circuitry, which powers the means for producing the radiation and the means for producing the absorption spectrum signal, could ignite hazardous or explosive vapors in the local area or vapors from the sample cell. For example, when the arrangements shown in FIGS. 1A, 1B and 1C are used for in-plant monitoring, the means for producing the radiation, the means for producing the absorption spectrum signal and the detector-cell are housed in separate compartments with the compartments being located adjacently to, and inline with, each other so that optical energy may be transmitted between the compartments. The need to locate these components near each other and within the line of sight of each other, yet separate them to meet safety codes substantially reduces the options available in locating an absorption detector within a processing environment.

A simple, compact, robust and inexpensive absorption detector is needed which features a detector-cell configuration that: (1) reduces bubble noise, (2) compensates for and utilizes the diffusion of radiation to maximize optical coupling, (3) allows easy access to the windows for inspection or replacement, (4) increases the sensitivity of the detector without increasing the dead zone of the sample cell and (5) provides for greater selectivity in locating absorption detector components to meet safety codes.

SUMMARY OF THE INVENTION

An object of this invention is to provide an absorption detector which has been adapted to reduce bubble noise and compensate for and utilize diffusion of source illumination in detecting absorption spectra for sample material flowing through a continuous-flow detector-cell.

Another object of the invention is to provide a detector-cell having easy access for inspection and/or replacement of a sample cell.

A further object of the invention is to provide a detector-cell which increases the sensitivity of the absorption detector without increasing the dead zone of a sample cell.

An additional object of the invention is to provide for greater selectivity in the locating of the absorption detector by enabling the detector-cell to be separately located from the electrical components of the detector.

Another object is to provide a method to detect continuous wavelength or single wavelength illumination that has been subjected to a continuous-flow of sample material which (1) reduces bubble noise, (2) compensates for and utilizes the diffusion of the illumination across the sample cell and (3) increases the sensitivity of the absorption measurement without increasing the dead zone of a sample cell.

In accordance with the objects of this invention, there is presented an absorption detector which uses a multi-branched optical guide to connect an electronics section with a detector-cell. The invention is adapted such that the detector-cell uses only a single connection location with the optical guide. The single connection location has two functions: (1) it acts as a location to provide optical energy to irradiate sample material within the detector-cell, and (2) its acts as a location to collect the absorption spectrum. By using the optical guide, it is possible to separate the detector-cell from the electrical components of the absorption detector for greater selectivity in locating components which make up the absorption detector to meet safety codes.

In preferred embodiments, a bifurcated optical guide is used. Each branch has a plurality of fibers (strands) which are combined at one end of the guide into a single bundle of fibers to provide a common end. In some embodiments, fiber ends of the common end may be either arranged in a random order or arranged so that the fiber ends from each branch are equally distributed across the common end. At the other end of the optical guide, the two branches are separated with the fibers of each branch being terminated at separate locations within the electronics section. One of the branches is located adjacently to a means for producing radiation to irradiate a species. The other branch is located adjacently to a means for producing an absorption spectrum signal.

The common end is connected to the detector-cell such that its fiber ends are located at a fixed location which is adjacent to an approximately vertically aligned continuous-flow sample cell. In one preferred embodiment, the sample cell has two flat parallel sides with the flat sides being approximately transverse to the fiber ends. A concave mirror is located on the opposite side of the sample cell from the optical guide connection.

The means for producing radiation for irradiating the sample material provides electromagnetic radiation (herein also referred to as: light, illumination, or optical energy) having continuous-wavelengths within the bandwidth of interest. The radiation is guided through its respective branch of the optical guide to the common end. There, the light diffuses across the sample cell, where some of the light is reflected back across the sample cell by the concave mirror to the common end. Within the sample cell, optical energy having certain wavelengths are absorbed to a greater extent than others, thereby forming an absorption spectrum. The concave mirror concentrates the light reflected from the mirror by reflecting the illumination toward the fixed location where it is collected as the absorption spectrum; thus, the mirror enables the detector-cell to be more efficiently utilize optical energy which has diffused across the sample cell. Also, the concave mirror at least doubles the optical path length of the optical energy, thereby increasing the sensitivity of the flow cell without increasing the dead zone of the sample cell. Additionally, the concave mirror in conjunction with the common end enables the detector-cell to utilize a single location adjacent the sample cell to both irradiate the sample and collect the illumination (the absorption spectrum) which has been subjected to the sample.

Reflected light striking the fiber ends of the branch associated with the means for producing an absorption spectrum signal is collected by fiber ends. The absorption spectrum is then guided to the electronics section where the absorption spectrum is converted to an electrical signal approximately proportional to the strength of the reflected wavelengths striking the fiber ends. The absorption spectrum signal may then be analyzed on a recorder for chemical composition or processed by various data processing methods, including but not limited to digitalization.

In preferred embodiments, the reflection characteristics of the mirror are selected in consideration of the location of the fiber ends (the fixed location), the mirror's location, and the refraction of light along the optical paths between the fiber ends and the mirror. In one highly preferred embodiment, the concave mirror is a spherical mirror with the fixed location for the fiber ends being at the center of curvature (the focal point) of the spherical mirror.

These and other objects and advantages of the present invention will no doubt become apparent to those of skill in the art after having read the following detailed description of the preferred embodiments which are contained herein and illustrated by various figures.

The invention encompasses the heretofore described preferred embodiments as well as the embodiments as are described hereinafter and as will be apparent to those of skill in the art.

BRIEF DESCRIPTION OF THE DRAWINGS

FIG. 1A is a simplified prior art illustration of an absorption detection arrangement having a "Z" flow cell for a sample cell used in a continuous-flow sampling system.

FIG. 1B is a simplified prior art illustration of an absorption detection arrangement having a "U" flow cell for the sample cell used in a continuous-flow sampling system.

FIG. 1C is a simplified prior art illustration of an absorption detection arrangement having a "vertical" flow cell for the sample cell used in a continuous-flow sampling system.

FIG. 2 is a simplified illustration showing the optical and electrical arrangement of one embodiment of the invention, the optical arrangement being shown in a simplified side view and the electrical arrangement being shown in block diagram.

FIG. 3 is a cross sectional illustration showing diffusion of optical energy across a sample cell.

DESCRIPTION OF THE EMBODIMENTS

Figure 4:
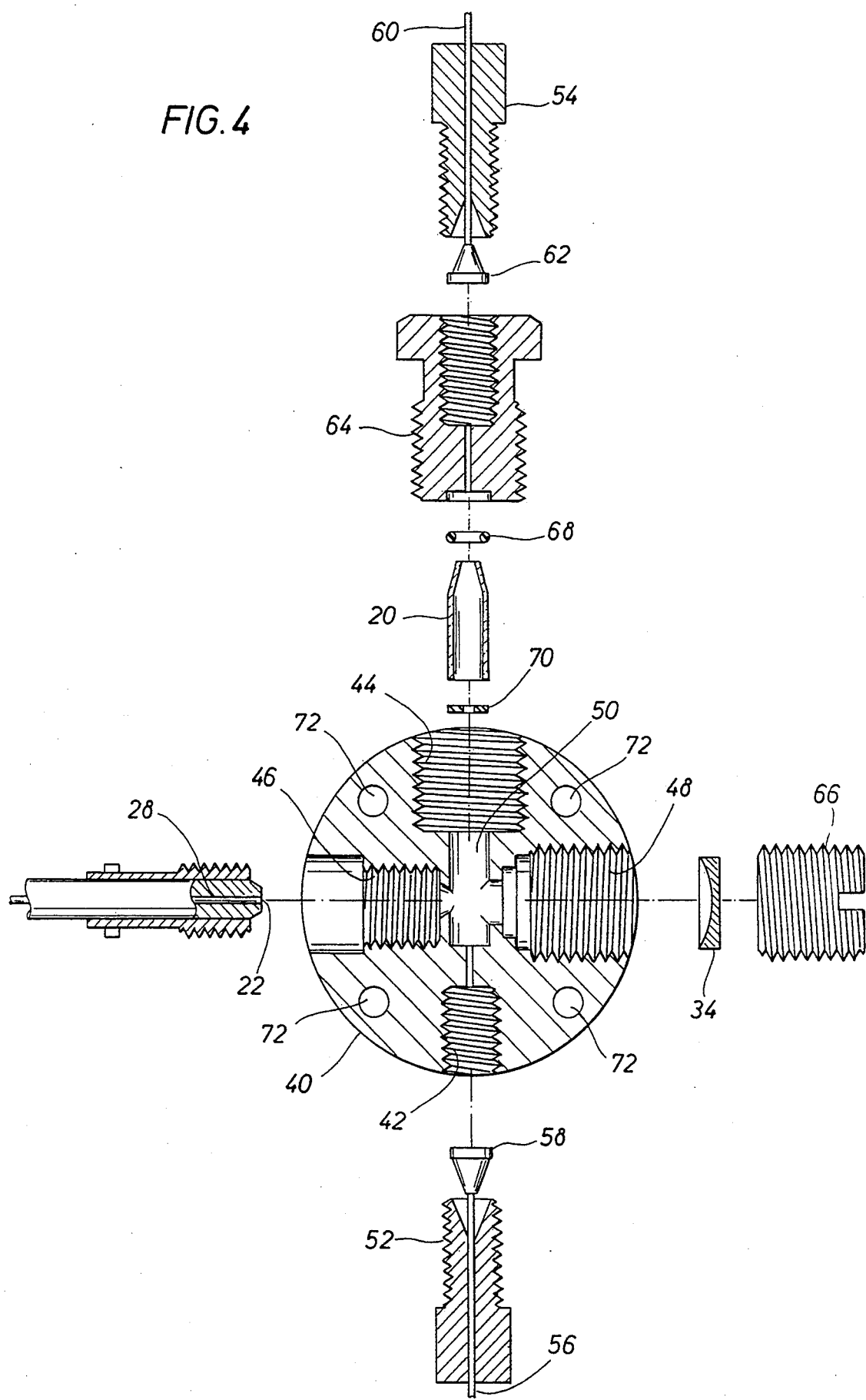
FIG. 4 is an exploded view showing a vertical cross section of one embodiment of the detector-cell assembly.

One preferred embodiment of an absorption detector adapted for continuous-flow detection and having a single point connection within the detector-cell for both the transmission and collection of optical energy is shown in FIG. 2.

FIG. 2 shows this embodiment to include a detector-cell (shown in simplified vertical cross section), an electronics section (shown in block diagram) and a bifurcated optical guide connecting the detector-cell with the electronics section.

The detector-cell includes an approximately vertically aligned, longitudinal, sample cell 20 having a bottom inlet and a top outlet. The openings enable the sampling system to supply a continuous-flow of sample material into the detector-cell. This approximately vertical alignment of the sample cell 20 prevents bubbles from remaining within it. A concave mirror is located on the opposite side of the flow cell from the optical guide connection.

In the embodiment of FIG. 2, a multibranched optical guide, preferably, has a plurality of fibers (strands) which are divided into two branches to form a bifurcated optical cable. Preferably, each branch also has a plurality of fibers, although it is possible for some embodiments of this invention to contain a single optical fiber in each branch. The fibers of the two branches are combined at one end of the optical guide into a single bundle of fibers having a common end 22. The common end is connected to the detector-cell such that its fiber ends 22 are held at a fixed location adjacent to the sample cell 20. At the opposite end of the optical guide, the two branches are separated to form two distal ends 23, and 24 for connection to the electronics section. One of the distal ends 23 is connected to the electronics section adjacent to a means for producing illumination for irradiating sample material. The fibers in this branch will be referred to as irradiating fibers. This branch guides irradiating light within its fibers from the electronics section to the detector-cell. The remaining distal end 24 is connected to the electronics section adjacent to a means for producing an absorption spectrum signal from collected illumination. Fibers within this branch will be referred to herein as collecting fibers. The fibers of this branch guide light which strikes their ends (the collecting fiber ends) from the detector-cell to the means for producing an absorption spectrum in the electronics section.

As mentioned previously, the combination of the means for producing radiation and the means for producing an absorption spectrum signal can be any combination known in the art of spectrophotometry for obtaining an absorption spectrum for analysis and includes, but is not limited to, the use of a monochromator in producing irradiating illumination, the scanning of an absorption spectrum over a single photodiode or the use of a photodiode array.

As the irradiating illumination leaves their respective irradiating fiber ends 22 to pass into the sample cell 20, the light diffuses. Some of the light, after traveling across the sample cell 20, is reflected back across by the concave mirror such that this reflected light strikes the fiber ends 22 at the fixed location.

Reflected light striking the collecting fiber ends is guided to the electronics section where the illumination is converted into an electrical signal (voltage or current) that is representative of the variations in the intensity of the different wavelengths in the absorption spectrum (reflected light) which strike the collecting fiber ends. The electrical signal may then be processed for various types of chemical analysis such as being displayed on a recorder or monitor or being digitalized for computer processing.

The use of the optical guide (fiber optic cable) enables the electrical components to be separated from the detector-cell; thus, the components no longer have to be near each other or within line of sight of each other and this also allows all of the electrical components to be placed in the same housing. In addition, sampling material which might present a substantial explosive hazard in the presence of electrical sparks could be separated completely from the electrical portions of the detector by using widely separated cabinets. Consequently, there is greater flexibility in meeting safety codes.

FIG. 3 is a cross-sectional illustration to show the diffusion of optical energy across sample cell 20 and how the single connection within the detector-cell for both irradiation of the sample and light collection enhances the utilization of optical energy in this invention. As mentioned previously, the fibers for each branch are combined to form a single bundle of optical fibers 28 having a common end 22. The common end is terminated within the detector-cell. The common end's fiber ends 22 are fixed in place next to the flow cell (sample cell) 20.

As optical energy (represented by 32 in FIG. 3) leaves the irradiating fiber ends, it diffuses as it crosses the sample cell 20. Much of the diffusion is dependent upon the characteristics of the optical fibers used. In typical fiber optic cable, depending upon the numerical aperture rating of the fiber, the angle of fan-out of the light as it leaves each fiber could range between 12 and 62 degrees. The numerical aperture rating also specifies the angles by which the fiber ends collect light. Additional diffusion occurs as the light crosses the cell. This additional diffusion results from refraction at each different material boundary, e.g., the walls of the sample cell and the sample material, beam spreading and scattering.

In typical operations, certain wavelengths within the bandwidth of the optical energy will be absorbed by the sample to a much greater extent than other wavelengths as it moves through the sample. When the light reaches the opposite side of the cell, this fanned-out (diffused) optical energy will encounter the concave mirror 34. The concave mirror will reflect much of the light (represented, in part, by 36 and 38 in FIG. 4) from a plurality of reflection points back into and across the sample cell such that the reflected optical energy is concentrated (or focused) in proximity to the fixed location.

Each reflection point on the mirror, will return reflected light approximately along the same path the light followed to strike the mirror. Upon encountering the different material boundaries, the reflected light will again be refracted such that the angle of this refraction will be approximately the reverse of the initial angle of refraction when the light first encountered that boundary. Since the light is not, in all cases, reflected exactly back along the path it took to arrived at the mirror or refracted during the recrossing at exactly the reverse of the initial refraction angles, all of the light does not return exactly to the same point it left the common end. However, because the light reflected from each reflection point is also subject to beam spreading and beam scattering, a substantial amount of reflected light will be concentrated (focused) near the fixed location where some of this reflected light will strike the collecting fiber ends.

This single point connection arrangement in conjunction with the concave mirror enhances light (optical energy) utilization in two ways. In one, it at least doubles the sensitivity of the detector without increasing the dead zone of the sample cell as compared to the typical detector-cell arrangements shown in FIGS. 1A, 1B and 1C. In the other, the design reduces light loses by using the concave mirror to intercept, reflect and concentrate (focus) the light such that substantially less light is lost from diffusion than in the previously mentioned prior art; thus, much of the illumination that was not directly on the axis between the sample cell windows was lost. Consequently, it was not collectable.

The total intensity of the light carried by each branch is based, in part, and assuming all else remains constant, upon the total number of fibers in each branch; thus, for example, if the amount of reflected light collected by and guided within the collecting branch is insufficient, the number of fibers in that branch may be increased. In embodiments where glass fibers cause substantial absorption at some of the wavelengths of interest in the absorption spectrum, other fiber material may be selected which may be made of silica, sapphire, fluoride or some other material, depending upon cost factors and the bandwidth of interest, to reduce attenuation.

In one embodiment, the strands of optical fibers in each of the two branches are randomized when combined to form the single bundle of fibers; thus, at the fixed location, the fiber ends are arranged in random order across the common end. In another embodiment, the fiber ends are arranged such that all of the fibers ends are approximately equally distributed across the common end. In still another embodiment, the fiber ends of one branch may be localized in the center of the common end with the fibers of the other branch forming an outer (concentric) circle of fibers. In other embodiments, the irradiating fiber ends could have a numerical aperture rating which reduces the fan out of light and the collecting fiber ends could have a numerical aperture rating which allows each fiber end to collect light from greater angles than the irradiating fiber ends.

In selecting the concave mirror of some embodiments, the concave mirror's reflection characteristics are selected with respect to the refraction characteristics of the material boundaries between the fiber ends and the mirror's location, e.g., the sample cell and the sampling material boundaries, the mirror's location, and the location and numerical aperture of the fiber ends. In one highly preferred embodiment, the concave mirror is a spherical mirror with the fixed location (the location of the common end) being center of curvature (the focal point) of the spherical mirror. Other embodiments are also possible, for example, in one embodiment, methods may be used to vary the fixed location of the common end in increments during calibration to identify the fixed location at which illumination on the collecting fiber ends for a particular mirror and/or sample material is maximized. In another, a lens may be used in conjunction with the sample cell to focus illumination to and from the fiber ends.

Figure 5:
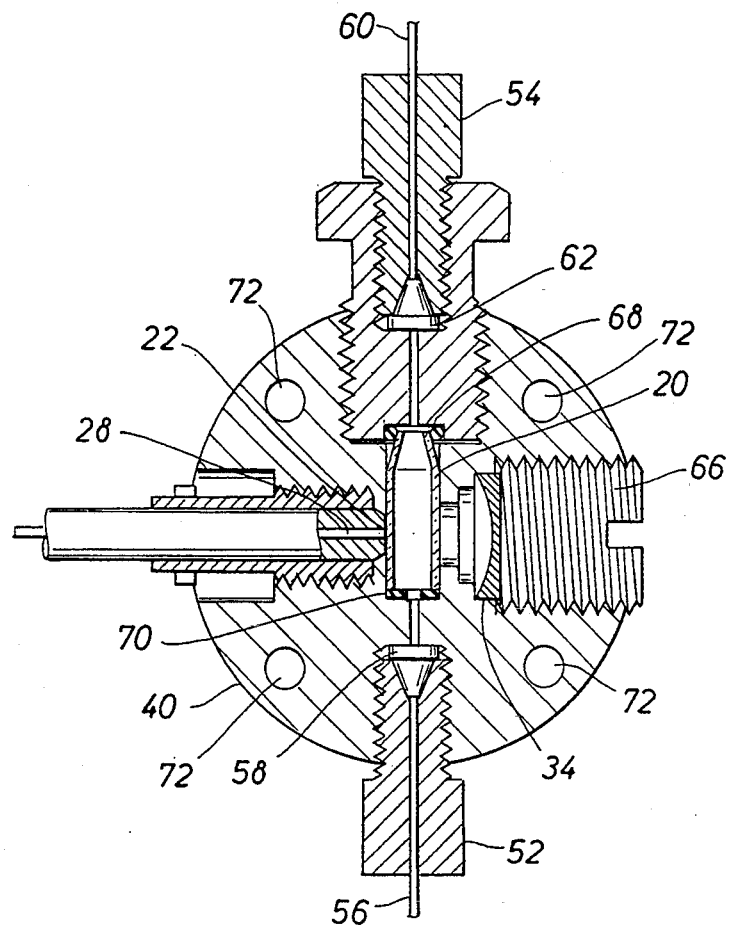
FIG. 5 is an assembled view of FIG. 4.

Referring now to FIGS. 4 and 5, FIG. 4 is an exploded vertical-horizontal cross sectional view of one embodiment of the detector-cell shown in simplified form in FIG. 2. And, FIG. 5 is an assembled cross sectional view of the detector-cell shown in FIG. 4. In some embodiments, the body 40 of the detector-cell may be machined from a single block of material. In one highly preferred embodiment, the body as well as most of the associated fittings are made from PEEK (polyetheretherketone). In other embodiments, it may be necessary to use other materials in order to meet the building code requirements due to particular explosive and fire hazards inherent in the substance being sampled with respect to the area where sampling is conducted.

Returning to FIGS. 4 and 5, the body 40 of the detector-cell contains four openings 42, 44, 46, and 48. All openings open into a central cavity 50 within the body which holds the sample cell 20. Openings 42 and 44 are used to connect the body to screw fittings 52, 54 which tie the detector-cell to a sample line. Sample line input fitting 52 includes a line 56 from the sample system running through the fitting and connecting to a ferrule 58. Output line fitting 54 has a similar arrangement with the output sample line 60 running through the fitting 54 and connecting to ferrule 62. However, fitting 54 does not connect directly to the body 40, but connects to a sample cell inspection fitting 64. This fitting 64 is used to provide access to sample cell 20 so that it may be easily inspected or replaced.

Opening 46 provides for the connection of the bundle of fibers 28 to the body 40 such that the common end's fiber ends 22 are held at the fixed location adjacent to the sample cell 20. In one preferred embodiment, opening 46 is machined to be compatible with a standard optical ST-type connector. The bundle of fibers 28 is then fitted with a standard optical ST-type connector to provide quick and repeatable re-connections of the optical guide to the detector-cell such that the fiber ends 22 are fixed with respect to the sample cell 20 and the concave mirror 34 mounted within opening 48. Screw 66 aligns and holds mirror 34 in place and allows removal of the mirror for inspection of the flow cell. The mirror may also be removed for change out of the mirror if different reflection characteristics are desired. For example, a change in the refraction index of the sampling materials may require a concave mirror with different reflection characteristic for reflecting and focusing the reflections. Additionally, the mirror may be removed for calibration checks. With the mirror removed, a determination of the light reflected from the sides of the flow cell may be possible so that adjustment (calibration) of the electronics section may be made for light which is not representative of the absorption spectrum of the sample.

Figure 6:
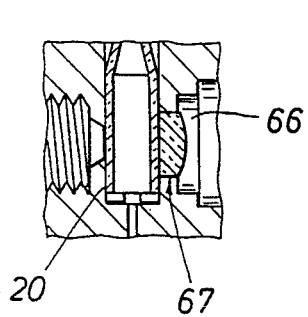
FIG. 6 is a partial side view of a detector-cell showing a different type of concave mirror than shown in FIG. 5.

FIG. 6 is a cross sectional partial view of the detector-cell showing another type of concave mirror 67 which may be used for reflecting light. In this embodiment, one side of the mirror rests against the sample cell 20 with a reflective surface being located on the far side of the mirror from the flow cell, i.e., a second side reflection coating mirror. Here the sample cell 20 aligns the mirror 67 and screw 66 holds it in place.

Figure 7C:
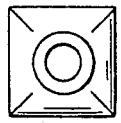
FIG. 7C is a top view of the flow cell embodiment of FIG. 7A.
Figure 7A:
FIG. 7A is a side view of one embodiment of a flow cell.
Figure 7B:
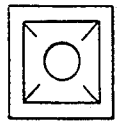
FIG. 7B is a bottom view of the flow cell embodiment of FIG. 7A.

One preferred embodiment of sample cell 20 is depicted in FIGS. 7A, 7B and 7C. FIG. 7A is a side view showing the sample cell to have a tapered top. In one representative embodiment, the straight wall portion of the sample cell is approximately 8 mm (millimeters) with the length of the tapered walls being approximately 5 mm. FIG. 7B is a bottom view of the embodiment of FIG. 7A. It shows this embodiment of the sample cell to have an approximately square bottom opening formed by the straight parallel wall portions. In this particular embodiment, the exterior cell walls are approximately 4.5 mm wide and the interior width of each cell wall is approximately 3.0 mm. FIG. 7C is a top view of the embodiment of FIG. 7A. The tapered walls and corners of this embodiment are increasingly rounded so that the top opening in the sample cell is circular. In the representative embodiment having the dimensions stated, the volume of the flow cell is approximately 80 micro-liters.

Returning to FIGS. 4 and 5, and using a sample cell similar to the embodiment of FIG. 7A, the round exterior top surface, shown by example in FIG. 7C, is sized so that a standard commercial "o-ring" 68 may be used to provide a pressure seal at the top of the sample cell 20. This ensures that the top of the sample cell may be quickly and easily sealed. Between the sample cell 20 and the bottom of chamber 50, a gasket 70 is used to provide the pressure seal. In some preferred embodiments the gasket may be glued to the bottom of the sample cell 20 to enhance the pressure seal.

Figure 8:
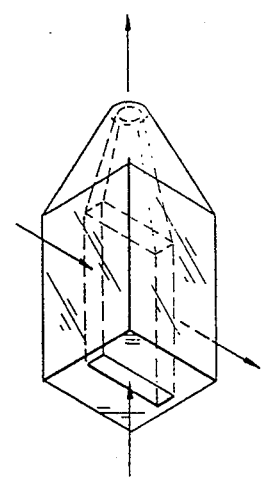
FIG. 8 is a perspective view of a sample cell having a narrow flow channel for sample material.

FIG. 8 shows in perspective another embodiment for a sample cell. One pair of arrows indicates the path of sample material though this flow cell from the bottom to the top. In this embodiment, the width of the sample cell's flow channel is narrowed to reduce the volume of the sample cell and decrease the dead zone. This is done by making the flow cell sides (walls) which do not face the mirror or the fiber ends thicker than the sides facing the common end. Another pair of arrows on FIG. 8 indicates a path for light to pass through the flow cell. In this embodiment, although the interior volume of the cell has been reduced, the sensitivity of the detector is not decreased since the length of the optical path length has not been shortened. Although the narrowing of the flow channel may reduce the amount of reflected light which may be detected, the use of flow cells having a standard exterior size and shape but different dead zones may enable a single detector-cell to be adapted quickly to provide absorption measurements based upon the size of the sample volumes available and the strength of the illumination provided.

In other embodiments, instead of being square shaped, the sample cell may be rectangular or have two rounded sides. However, it is highly preferred that the sample cell have two parallel flat sides with the flat sides being approximately transverse to the light radiation emerging from the common end.

In some embodiments, the sample cell is made from annealed quartz. In other embodiments, other materials may be used which have the necessary transparency to allow enough light to be transmitted and reflected across the sample cell. Additionally, anti-reflective coatings may be used to reduce the amount of reflection from the sample cell walls into the common end.

Returning to FIG. 4, preferably, chamber 50 is milled such that the sample cell 20 is self-aligning within the chamber. In one preferred detector-cell embodiment having a sample cell with two parallel flat sides, the chamber is milled to ensure the proper alignment of the sample cell with the fiber ends 22 so that the flat sides are approximately transverse to optical energy exiting the fiber ends 22. When the chamber is milled for self alignment, it is a simple matter to unscrew the fitting 64, to inspect or replace the sample cell and to have assurance that the cell is properly aligned with the fiber ends and the mirror. The implementation of the self aligning embodiment described in FIGS. 4 and 5 would allow a person to inspect the sample cell without tools since these associated fittings of the illustrated detector-cell may be removed by hand.

Additionally, since this invention enables the electronics section to be separated from the detector-cell, in certain applications, e.g., FIA (flow injection analysis), the detector-cell may be made portable so that it may be moved from one location to another for convenience in a laboratory or for sampling at various processing locations without having to move the accompanying electronic section or its associated recorders or computer interface. In one embodiment, instead of using mounting holes 72, a magnet is placed on the detector-cell so that it may conveniently be supported without the necessity of mounting it to a wall or work bench by screws or other mounting methods.

Although, the embodiments presented have been discussed with respect to liquid samples, the embodiments of this invention may also be adapted to be used with a continuous-flow gas sampling system. Additionally, embodiments of this invention could be used to provide a dual-wavelength absorption detector by isolating a reference wavelength and a measuring wavelength from the detected absorption spectrum or the absorption spectrum signal and applying the Lambert-Beer Law to the two wavelengths. In addition, dual-wavelength detection may be obtained by guiding irradiating illumination from two pulsed LEDs (Light Emitting Diodes) within an irradiating branch or two separate branches of an optical guide to the detector-cell of this invention, a dual-wavelength absorption measurement could be obtained. One LED is selected to provide radiation at the reference wavelength and the other LED provides radiation at the measuring wavelength. When the LEDs are pulsed alternately, a separate branch having collecting fiber ends may then guide the pulsed reflected wavelengths of radiation away from the detector-cell to an electronics section. There the wavelengths could be converted to an electrical signal and the signals compared in accordance with the Lambert-Beer Law to provide a value of absorbance for the species.

While several embodiments of the invention have been shown and described, it will be understood that the invention is not limited thereto since many modifications may be made and will become apparent to those of skill in the art.

What is claimed:

1. A detector-cell for use in continuous-flow chemical analysis which uses a single location to both irradiate sample material with electromagnetic radiation and collect the radiation which has been subjected to sample material, the detector-cell having the additional attributes of providing for inspection, cleaning and replacement of detector-cell components to improve detector-cell performance when the response of the detector-cell components has been reduced by contact with the sample material or by a change in the characteristics of the sample material and being substantially free of bubble induced noise, the detector-cell being adapted to connect to a sample line having the capability of providing a continuous stream of material for sampling, the sample line including an inlet sample line, an outlet sample line and a means for flowing sampling material into the inlet sample line, the detector-cell comprising:
- a detector-cell body, the body having four openings connecting to a central cavity within the body, the four openings including a top opening and a bottom opening located opposite each other and a third opening and a fourth opening located opposite each other and approximately transverse to the top and bottom openings;
- a means for connecting the top opening to the outlet sample line;
- a means for connecting the bottom opening to the inlet sample line wherein flow from the sample line is from bottom to top through the detector-cell;
- a longitudinal sample cell having two flat parallel sides, the sample cell being located within the central cavity such that its longitudinal length is aligned approximately vertical, the sample cell including a bottom inlet and a top outlet which are functional to allow sample material from the sample line to flow through the sample cell, wherein bubbles are swept out of the sample cell by an upward flow of the sample material thereby preventing entrapment of bubbles within the sample cell and reducing the ability of the sample cell to cause the bubble induced noise;
- wherein the means for connecting the top opening to the sample line includes a means for removing the sample cell through the top opening for inspection, cleaning and replacement;
- a multi-branched optical guide having a common end, the guide being attached to the third opening such that the common end is located at a fixed location within the body and adjacent to one of the flat parallel sides of the sample cell, wherein a first branch of the optical guide is functional for guiding irradiating electromagnetic radiation from outside the detector cell to the common end, and wherein a second branch of the optical guide is functional for guiding collected radiation from the common end to the outside of the detector-cell;
- a concave mirror located within the fourth opening and adjacent to the other flat parallel side of the sample cell such that the mirror is on the opposite side of the sample cell from the fixed location;
- a means for securing the mirror within the fourth opening so that the mirror is removable to allow the mirror to be inspected and replaced and to allow inspection of the sample cell through the fourth opening;
- wherein the common end at the fixed location is functional for transmitting the electromagnetic radiation across the sample cell's width such that the radiation diffuses as it crosses the sample cell and encounters the mirror; and
- wherein the concave mirror is functional to reflect and to focus portions of the diffused radiation back across the sample cell to the common end such that it is concentrated at the fixed location for collection, wherein the portions of the diffused radiation striking the common end are collected and guided outside the detector-cell, thus the detector-cell is functional for subjecting the collected radiation to the sample material within the sample cell twice, thereby doubling the detector-cell's optical path length within the sample material without increasing the sample material's volume within the sample cell.

2. The detector-cell of claim 1 also including an o-ring and wherein the sample cell has a tapered top, the tapered top having a round exterior top surface such that the o-ring may provide a pressure seal between the tapered top and the means for connecting the top opening to the sample line.

3. The detector-cell of claim 1 wherein the central cavity and the sample cell have dimensions which are sized such that when the sample cell is positioned within the central cavity the cavity's dimensions confine the sample cell in such a manner that the sample cell is aligned within the cavity to ensure a proper alignment of the sample cell with respect to the fixed location, the mirror and the means for connecting the top opening to the sample line.

4. The detector-cell of claim 3 also including a second sample cell having an optical path length which is approximately the same as said sample cell, an external exterior size which is the same as said sample cell and a different sample material volume than said sample cell, and wherein the sample material volume within the detector-cell may be changed by exchanging the sample cell within the detector-cell with the second sample cell.

5. The detector-cell of claim 1 wherein the concave mirror is a spherical mirror and the fixed location is located at the center of curvature of the spherical mirror.

6. The detector-cell of claim 1 wherein the sample cell is made of annealed quartz.

7. The detector-cell of claim 1 wherein the detector-cell body is made of polyetheretherketone.

8. The detector-cell of claim 1 wherein the means for connecting the top and bottom openings to the sample line includes screw connectors which allow connection to the sample line to be made by hand.

9. A continuous-wavelength absorption detector for use in continuous-flow chemical analysis, the detector being adapted to both irradiate a species with radiation over a bandwidth of interest and collect an absorption spectrum of the irradiated species from a single location, the detector also being adapted to connect to a sample line having the capability of providing a continuous stream of sampling material containing the species for sampling, the sample line including an inlet sample line, and outlet sample line and a means for flowing sampling material into the inlet sample line, the absorption detector also having the additional attributes of providing for inspection, cleaning and replacement of certain detector components to improve detector performance when the response of these certain components has been reduced by contact with the sample material or by a change in the characteristics of the sample material and of being substantially free of bubble induced noise, the detector comprising:
- a means for producing radiation having the bandwidth of interest for irradiating the species;
- a means for producing an absorption spectrum signal from an absorption spectrum which results from irradiating the species with the radiation;
- a detector-cell, the detector-cell includes a detector-cell body having four openings connecting to a central cavity within the body, a longitudinal sample cell and a mirror;
- the four openings include a top opening and a bottom opening located opposite each other and a third opening and a fourth opening located opposite each other and approximately transverse to the top and bottom openings;

a means for connecting the top opening to the outlet sample line;

a means for connecting the bottom opening to the inlet sample line wherein flow from the sample line is from bottom to top through the detector-cell;

the longitudinal sample cell has two flat parallel sides and is located within the central cavity such that its longitudinal length is aligned approximately vertical, the sample cell also including a bottom inlet and a top outlet which are functional to allow sample material containing the species to flow from the sample line through the sample cell, wherein bubbles are swept out of the sample cell by an upward flow of the sample material thereby preventing entrapment of bubbles within the sample cell and reducing the ability of the sample cell to cause the bubble induced noise;

wherein the means for, connecting the top opening to the sample line includes a means for removing the sample cell through the top opening for inspection, cleaning and replacement;

a multi-branched optical guide having a common end, the optical guide being attached to the third opening such that the common end is located at a fixed location within the body and adjacent to one of the flat parallel sides of the sample cell, the multi-branched optical guide including a first branch and a second branch, wherein the first branch of the optical guide has a distal end which is terminated near the means for producing radiation, the first branch being functional for guiding the radiation from the means for producing radiation to the common end, and wherein the second branch of the optical guide has a distal end which is terminated near the means for producing the absorption spectrum signal;

the concave mirror is located within the fourth opening and adjacent to the other flat parallel side of the sample cell such that the mirror is on the opposite side of the sample cell from the fixed location;

a means for securing the mirror within the fourth opening so that the mirror is removable to allow the mirror to be inspected and replaced and to allow inspection of the sample cell through the fourth opening;

wherein the common end at the fixed location is functional for transmitting the radiation to irradiate the species, the radiation being transmitted into and across the sample cell such that the radiation diffuses at it emerges from the common end; and wherein the concave mirror is functional to reflect and focus portions of the diffused radiation back across the sample cell such that some of these portions of the reflected radiation are concentrated near the fixed location such that they strike the common end thereby providing the absorption spectrum at the common end, and wherein the common end is also functional to collect the absorption spectrum and guide the absorption spectrum outside the detector-cell on the second branch of the guide to the means for producing the absorption spectrum signal, whereby the absorption spectrum is converted into an absorption spectrum signal.

10. The continuous-wavelength absorption detector of claim 9 also including an o-ring and wherein the sample cell has a tapered top, the tapered top having a round exterior top surface such that the o-ring may provide a pressure seal between the tapered top and the means for connecting the top opening to the sample line.

11. The continuous-wavelength absorption detector of claim 9 wherein the central cavity and the sample cell have dimensions which are sized such that when the sample cell is positioned within the central cavity the cavity's dimensions confine the sample cell in such a manner that the sample cell is aligned within the cavity to ensure a proper alignment of the sample cell with respect to the fixed location, the mirror and the means for connecting the top opening to the sample line.

12. The continuous-wavelength absorption detector of claim 11 also including a second sample cell having an optical path length which is approximately the same as said sample cell, an external exterior size which is the same as said sample cell and a different sample material volume than said sample cell, and wherein the sample material volume within the detector-cell may be changed by exchanging the sample cell within the detector-cell with the second sample cell.

13. The continuous-wavelength absorption detector of claim 9 wherein the concave mirror is a spherical mirror and the fixed location is located at the center of curvature of the spherical mirror.

14. The continuous-wavelength absorption detector of claim 9 wherein the sample cell is made of annealed quartz.

15. The continuous-wavelength absorption detector of claim 9 wherein the detector-cell body is made of polyetheretherketone.

16. The continuous-wavelength absorption detector of claim 9 wherein the means for connecting the top and bottom openings to the sample line includes screw connectors which allow connection to the sample line to be made by hand.

* * * * *